United States Patent
Leverne Harris

(10) Patent No.: US 6,512,212 B1
(45) Date of Patent: Jan. 28, 2003

(54) HEATER WITH REMOVABLE CARTRIDGE

(75) Inventor: J. C. Leverne Harris, Rockwood (CA)

(73) Assignee: Thermomedics International Inc., Rockwood (CA)

( * ) Notice: Subject to any disclaimer, the term of this patent is extended or adjusted under 35 U.S.C. 154(b) by 0 days.

(21) Appl. No.: 09/702,031

(22) Filed: Oct. 30, 2000

(51) Int. Cl.[7] ................................................ H05B 6/10
(52) U.S. Cl. ...................................... 219/628; 392/470
(58) Field of Search ................................ 219/628, 629, 219/630, 635, 602; 392/470, 465, 477, 493; 428/35.7, 36.91, 35.9

(56) References Cited

U.S. PATENT DOCUMENTS

| | | | |
|---|---|---|---|
| 4,464,563 A | * 8/1984 | Jewett | ......................... 392/470 |
| 4,791,262 A | 12/1988 | Ando et al. | |
| 4,847,470 A | * 7/1989 | Bakke | ......................... 392/470 |
| 4,855,552 A | 8/1989 | Marceau et al. | |
| 5,101,086 A | 3/1992 | Dion et al. | |
| 5,125,069 A | * 6/1992 | O'Boyle | ...................... 392/465 |
| 5,216,215 A | 6/1993 | Walker et al. | |
| 5,319,170 A | 6/1994 | Cassidy | |
| 5,381,510 A | * 1/1995 | Ford et al. | ................... 392/470 |
| 5,401,939 A | 3/1995 | Iguchi et al. | |
| 6,078,032 A | 6/2000 | Miller et al. | |

FOREIGN PATENT DOCUMENTS

WO    WO 97 34445 A    9/1997

OTHER PUBLICATIONS

Nakamura Akio; Heater For Fluid In Pipe; Patent Abstracts of Japan; Publ. 56127139; Oct. 6, 1981.

* cited by examiner

*Primary Examiner*—Teresa Walberg
*Assistant Examiner*—Quang Van
(74) *Attorney, Agent, or Firm*—Klauber & Jackson

(57) ABSTRACT

A heater device that is particularly adapted for use in supplying fluids to a living entity, such as a human or an animal. The heater is a transformer and includes a core, a primary winding and a secondary. The core is preferably a pair of E-shaped core sections, each having outer legs and an inner leg, with the outer legs being longer than the inner legs. The core thus forms a receiver opening intermediate the inner legs that slidingly receives a self-contained cartridge enclosing the secondary. The secondary is a planar, tubular conduit shaped in the configuration of an elongated loop and having an inlet for receiving fluid and an outlet for discharging that fluid at an elevated temperature. The extending ends of the outer and inner legs of each core sections face each other and form a receiver opening intermediate the inner legs. The cartridge is insertable and removable from the opening. When inserted, the secondary is in the magnetic flux created by an alternating power supplied to the primary windings and the secondary is shorted out to convert that magnetic flux into heat to warm the fluid passing through the secondary to the desired temperature. The cartridge is easily removable for cleaning and/or replacement.

33 Claims, 5 Drawing Sheets

US 6,512,212 B1

HEATER WITH REMOVABLE CARTRIDGE

BACKGROUND OF THE INVENTION

This invention relates to a device to carry out the heating of fluids to a predetermined temperature and, more particularly, to a device that can efficiently heat medical fluids for introduction into a living entity such as an animal or a human patient.

In general, there are certainly many methods and devices for heating fluids including the use of resistance heaters as well as combustion heaters, heat exchange units and the like. One type of heater that has been disclosed for use in heating of fluids is by means of a transformer having a primary and a secondary. Basically, in such devices, the secondary comprises a conduit through which the fluid to be heated passes and that secondary is shorted out so as to convert the magnetic flux created by an alternating current through the primary into heat in the secondary. Accordingly, as the fluid passes through the secondary, it is heated and can be used for various purposes. A transformer type of fluid heater is shown and described in U.S. Pat. No. 6,078,032 of Miller et al where the heating device is utilized to heat water in the preparation of coffee.

In the field of medical uses, heaters are normally used to warm a fluid for infusion into a living being, albeit a human patient or an animal. Typically, the fluid used in such practice are fluids such as plasma, whole blood for trauma use, fluids needed during organ transplants, frozen plasma that needs to be heated up and the like. With the introduction of these fluids into a living being, it is obvious that there is a need for precise control of the temperature as well as to be able to maintain that temperature constant during different flows of the fluid and even during the stoppage of that flow, that is, the temperature must be controlled even during a stoppage of the flow within the heater so that no excessive temperatures are reached during any conditions of the flow or operation of the heating device including, during a cycle where the flow is halted for a period of time and then restarted.

In addition, the heater for such uses must provide a uniform heating to the fluid itself as any hot spots or areas where an excessive temperature may contact the fluid can cause a degrading of the fluid and render that fluid unfit for the intended purpose. For example a hot spot may give rise to an excessive temperature and can destroy protein that is in the fluids being delivered. In addition, of course, it is important in the use of such heater devices for medical uses that the surfaces or any materials that come in contact with the fluids circulating to and from the patient be capable of being easily sterilized in preparation for subsequent patients and to prevent cross contamination. Certainly, in the aforedescribed Miller et al patent, there is no practical way to facilitate such cleaning and sterilization process with that disclosed heater device.

Accordingly, it would be advantageous to provide a heater of such fluids that is efficient, safe for use without fear of electrical shock, provide an even, uniform heating of the fluid and yet have sufficient capacity to heat the fluid to the desired temperature at the flows utilized in that use.

SUMMARY OF THE INVENTION

Thus, in accordance with the present invention, there is provided a heating device for the heating of fluids that provides a uniform heat to the fluid and can be operated at the precise temperatures needed for warming a supply of fluid to be used for the infusion of an entity including a living animal or human. In the present invention the heater itself is a transformer where the secondary includes a path for the flow of the fluid. The preferred transformer core comprises two E-shaped ferrite core sections that meet together with the open ends of the E-shaped core sections coming together. The E-shaped configuration provides two outer legs and an inner leg of each of the E-shaped core sections and the inner legs are shorter that the outer legs of each core section. There is an opening formed in-between the two E-shaped sections of the primary due to the shorter length of the inner leg of the of the E-shaped core sections.

The primary windings are wound around both of the E-shaped core sections equally, that is, there are preferably an equal number of windings around each of the E-shaped core sections and a wire loop connects the two sets of windings. In the preferred embodiment, both E-shaped core sections are biased toward each other. Ferrite blocks are also preferably located adjacent and in contact with the external sides of the E-shaped core sections in order to made sure there is continuity between the core sections even when the outer legs of the core sections are not fully in contact with each other. By passing a high frequency electrical current through the primary, an alternating magnetic field is created in the secondary.

The secondary of the transformer comprises a planar singular, elongated tubular loop having an inlet and an outlet and a plurality of curves and corners to break up any laminar flow pattern of fluid to insure a thorough mixing of the fluid, thereby creating a isothermic fluid flowing from the outlet at the desired elevated temperature. Each curve is formed to have an increased diameter in order to slow the velocity of the fluid passing through the curves and to reduce the hydraulic gradient formation.

The secondary itself is a high resistivity, thin walled ferrous material and is encased within a plastic material preferably polyetheramide to form a cartridge that can be easily inserted and removed from an operative position in the opening formed between the two core sections. The material of the secondary is preferably stainless steel. The elongated loop is shorted out at or near the inlet and outlet by welding in order to convert the magnetic flux created by the high frequency primary into heat in the secondary.

By the use of the aforedescribed construction, the plastic encased secondary can be removed from the E-shaped core sections for cleaning, such as autoclaving, and the secondary returned to the position within the opening between the core sections, or an alternate secondary cartridge can be inserted while the other secondary cartridge is being cleaned or repaired.

A ferrite inset is also incased in the plastic along with the secondary and is located in the inner area of the elongated looped configuration of the secondary. The addition of the ferrite insert aids in the uniform distribution of the magnetic flux and thus enhances the heating effect of the overall device. When the secondary is inserted into the opening as the heat device is functioning, the bias forcing the two core sections together to assure that the secondary is retained in close proximity to the ferrite core sections to aid in the efficiency of the device.

The interior surface of the secondary is preferably coated with and hermetically sealed by a layer of a material bonded to that surface. The material has a high dielectric insulation, has a low potential for triggering an immune response and has very low thrombogenic properties. In the preferred embodiment, the coating material is a vacuum deposited layer of parylene.

These and other features and advantages of the present invention will become more readily apparent during the following detailed description of the invention taken in conjunction with the drawings herein.

DETAILED DESCRIPTION OF THE INVENTION

Figure 1:
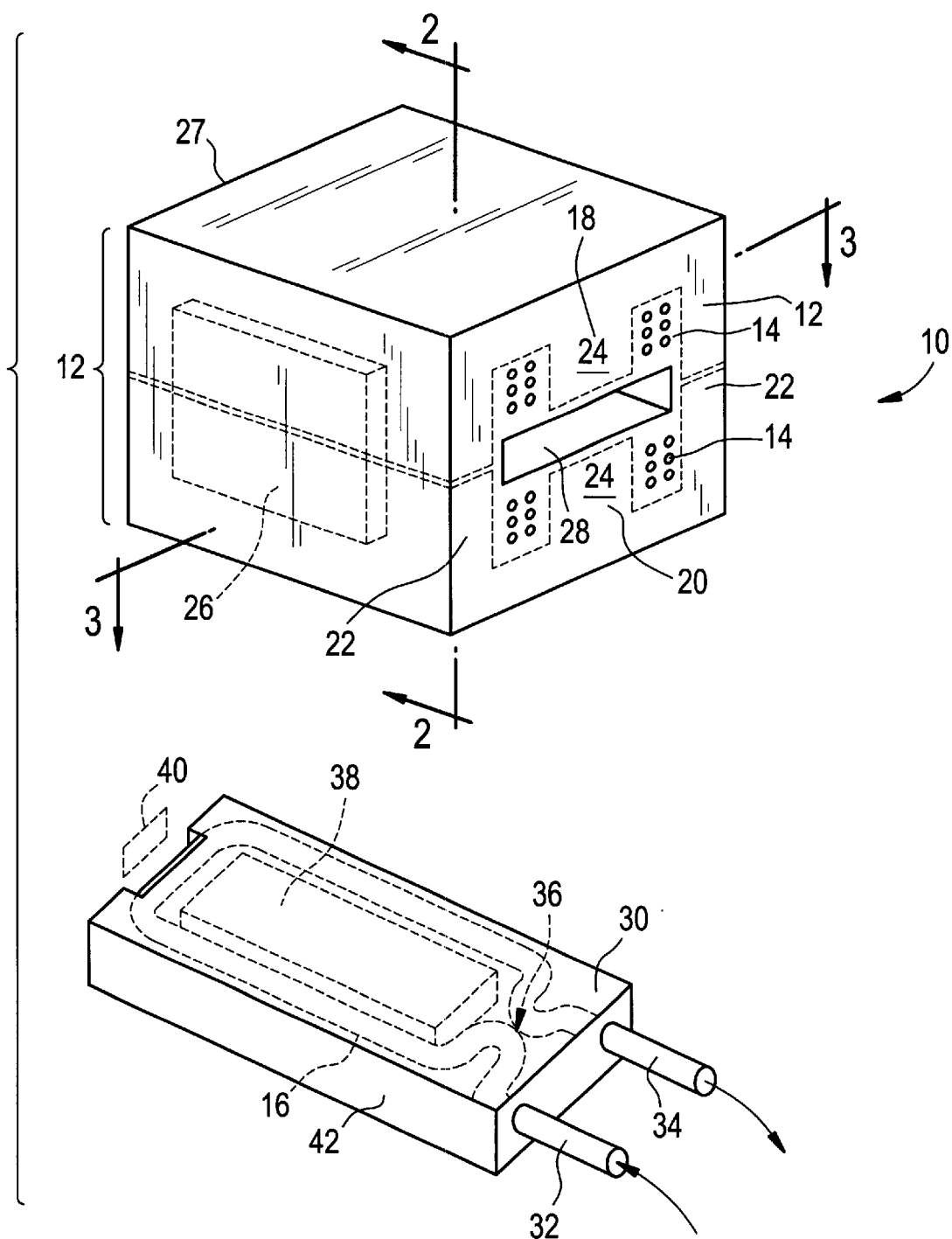
FIG. 1 is a perspective assembly view of a heating device constructed in accordance with the present invention.
Figure 2:
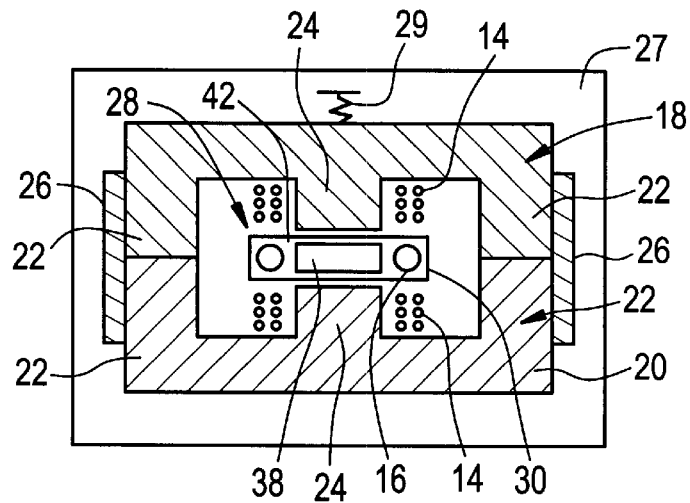
FIG. 2 is a cross sectional view taken along the line 2—2 of FIG. 1.

Turning first to FIGS. 1 and 2, there is shown, in FIG. 1 a perspective assembly view, and in FIG. 2, a cross sectional view taken along the line 2—2 of FIG. 1 and which shows the present invention that is a heating device 10 for heating fluid, and in particular, fluid to be introduced into a living entity such as an animal or a human patient. The heating device 10 is a transformer comprising a primary made up of a core 12 having primary windings 14 and a secondary 16 with a relationship that will be described.

Taking first the primary, the core 12 is comprised of E-configured core sections 18 and 20 that are each formed with outer legs 22 and inner legs 24, with the inner legs 24 being of shorter length than the outer legs 22. The outer legs 22 and the inner legs 24 of each of the core sections 18, 20 face each other such that the outer legs 22 of one core section 18 will be in contact, or closely contiguous, with the outer legs 22 of the other core section 20. In the preferred embodiment the surface area of contact of the outer legs 22 added together is about the surface area of the contact between the inner legs 24.

A pair of transition spacers 26 (only one of which is shown in FIG. 1) are located along the outer, lateral surface of the core sections 18, 20 and in contact with that outer surface so as to span both of those core sections 18, 20 and provide a continuous path for the magnetic flux even if, due to the various tolerances in the construction of the heating device 10. There is a gap or space that remains between the outer legs 24 of each of the core sections 18, 20. Accordingly, in the event there is a gap or space between the otherwise mating outer legs 22 of the respective core sections 18, 20, the use of the spacers 26 of a low magnetic permeability material, such as ferrite, will provide a continuous and smooth path for the magnetic flux to pass between the core sections 18, 20. The transition spacers 26 are comprised of a ferromagnetic material to enhance the flux continuity.

As can be seen, the primary windings 14 surround the inner leg 22 of each core section 18, 20 and it is preferred that the number of the primary windings 14 of each of the core sections 18, 20 be the same, that is, in the embodiment shown there are six primary windings 14 about each of the core sections 18, 20 so that the configuration of half of the primary windings 14 above the secondary 16 and half of the primary windings 14 below the secondary 16 provide optimal coupling of the induced current.

The material for the core 12 in the preferred embodiment, is a ferrite material, preferably a ceramic sintered iron, however it could be other material such as steel. The entire core sections 18, 20 as well as the spacers 26 after being properly positioned are enclosed within a polyurethane foam material 27 to maintain the heating device 10 as a compact, transportable unit. In the assembly of the overall heating device 10, there also can be a spring bias 29, (shown schematically in FIG. 2) exerted to bias the core sections 18, 20 toward each other and which bias aids in the insertion and removal of the secondary 16 as will become clear.

Thus, due to the shapes of the E-configured core sections 18, 20 and the differing lengths of the inner legs 22 and outer legs 24, there is formed a receiver opening 28 intermediate the two core sections 18, 20.

Therefore, turning to the secondary 16 of the transformer, the secondary 16 is formed within a cartridge 30 that is configured and shaped so as to fit into the receiver opening 28 so that the secondary 16 will be located intermediate the core sections 18, 20 and be influenced by the magnetic flux produced by the alternating current passing through the primary windings 14. The secondary 16 itself is a generally planar, curved conduit formed in the shape of an elongated loop and having an inlet 32 and an outlet 34. The inlet 32 is used to receive fluid and the outlet 34 delivers that fluid at an elevated temperature to a desired end use as will be explained.

The secondary 16 is shorted out at 36 i.e the conduit is affixed together, such as by welding, at that point and which is near or adjacent to the inlet 32 and the outlet 34. The shorting out of the secondary 16 serves to capture and convert the magnet flux created in the heating device 10 by the alternating current in the primary that creates an induced current which is trapped in the wall of the secondary 16 and converted into heat in the secondary 16 in order to warm the fluid that passes through the secondary 16.

A ferrite insert 38 is also located within the interior of the elongated loop of the secondary 16 and which also contributes to the efficiency in heating the fluid that passes through the secondary 16 and, as will be explained, compensates for the air gap that inherently occurs as a result of the plastic encasement of the secondary 16 to form the cartridge 30.

The entire secondary 16 as well as the ferrite insert 38 is preferably covered and encased by a thin film of plastic material 42 such as a glass-filled polyetherimide available commercially under the trademark Ultem. That material is preferred since it can be autoclaved for cleaning, resists high temperatures, has the requisite strength for the purpose and has low thermal coefficient of expansion. Other materials having similar properties could also be used. Thus, the secondary 16, is formed as a compact cartridge 30 and, as can now be seen, can readily be inserted into and removed from the receiver opening 28 so that the secondary 16 can be removed from the receiver opening 28 for cleaning and another similar secondary cartridge 30 then inserted into the receiver opening 28 during that cleaning process so as to get the maximum usable time from the heating device 10, and minimum of down time.

Figure 3:
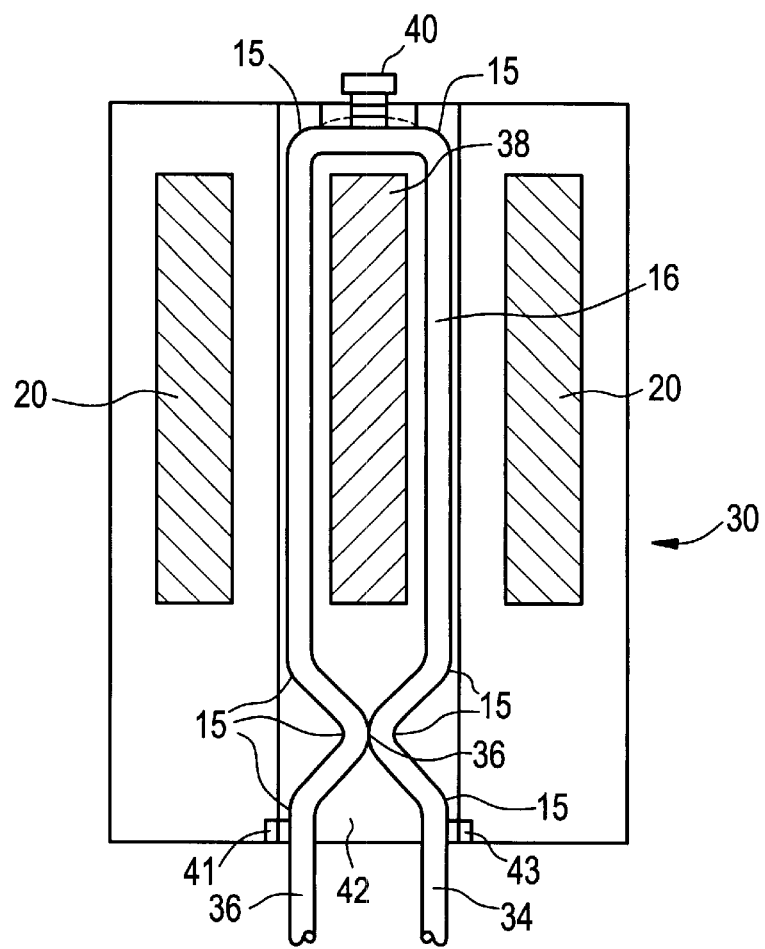
FIG. 3 is a vertical sectional view taken along the line 3—3 of FIG. 1.

Turning now to FIG. 3, there is shown a cross sectional view of the present heating device 10 taken along the line 3—3 of FIG. 1 and which shows, more clearly, the preferred configuration of the secondary 16. As can be seen, the secondary 16 has a plurality of abrupt curves 15, that is, there are at least six abrupt curves 15 that exceed an angular curvature of about 45 degrees and thus the overall secondary 16 provides a tortuous path for the fluid passing therethrough. The use of a plurality of such abrupt curves 15 in the basically planar elongated loop configuration aids in the mixing of the fluid passing through the secondary 16 and breaks up any laminar flow patterns so as to insure a thorough mixing of the fluid and thereby provide an isothermic fluid at the outlet 34 after passing through the secondary 16.

The material for the secondary 16 is also an important consideration and it is preferred that the material be a thin walled ferrous material having a thickness of about 4–6 mils, more preferably stainless steel. The use of a thin walled secondary 16 is critical for two reasons. First, the thin walled conduit provides a very low overall mass and hence has a low thermal inertia whenever the flow ceases, that is, there is no significant thermal bump in the event the fluid is caused to remain motionless in the secondary 16 for a period of time and is again caused to flow. The lack of a thermal bump allows the heater device 10 to deliver the fluid without a upward rise in temperature upon restart after that motionless period of time. Second, the thin wall of the secondary 16 has a low thermal gradient across its thickness, i.e. the difference in the temperatures between the outside skin temperature and the inside skin temperature of the walls of the secondary 16 is extremely low, in the order of about 6 degrees F irrespective of the rate of heating.

In addition, the use of a high resistivity material for the secondary of a ferrous material also allows for more efficient capture of the B component of the electromagnetic wave and increases the heat of resistance when the secondary containing the induced current is shorted.

It is also preferred that the internal surface of the secondary 16 be coated with a material to enhance the flow and to exhibit certain preferred characteristics and thus that internal surface is hermetically sealed with an agent bonded thereto which has a high dielectric insulation, a low potential for triggering an immune response and very low thrombogenic properties. As a preferred material, parylene can be vacuum deposited on the internal surface of the secondary 16. An alternate material can be silicone and in any instance, it is preferred that the thickness of the internal coating be about 1 mil or less.

The shorted point 36 of the secondary is preferably near the inlet 32 and the outlet 34 and can be a welded connection to effect the short of the secondary 16. It is also advantageous that the short or weld area be 2 times the cross section area of the wall of the secondary 16. If that weld or contact point is too small an area, there can be created a high resistance across the weld and create a hot spot such that the fluid, again, can reach an unacceptably high temperature. Therefore, by making the weld area sufficiently large with respect to the cross sectional area of the conduit of the secondary 16, that weld offers a relatively low resistance to the passage of current across the short and no hot spot is created.

Infrared sensors 40, 41 and 43 are also employed to sense the temperature of the secondary 16 and can be a conventional temperature sensors that directs an infrared beam onto a blackened surface on the secondary 16 to detect the temperature of the secondary 16. A suitable commercial temperature sensor is available from the Dexter Research Center, Inc. of Dexter, Mich. as a thermopile detector. As a feature, however, one infrared sensor 40 is preferably located within the foam material 27 of the heating device at the inner end of the receiver opening 28 and the temperature sensors 41 and 43 are located at the entrance to the receiver opening 28 at the lateral sides thereof. Since the temperature sensors 40, 41 and 43 all operate to reflect the infrared energy off a blackened area of the secondary 16, there are openings in the plastic material 42 of the cartridge 30 that align with the respective temperature sensors 40, 41 and 43 when the cartridge 30 is located within the receiver opening 28 in its operative position.

Thus, the temperature sensor 41 senses the temperature of the secondary 16 at its inlet 32, the temperature sensor 43 senses the temperature of the secondary 16 at its outlet 34 and the temperature sensor 40 senses the temperature of the secondary 16 at a point about equidistant between the inlet 32 and the outlet 34. Accordingly, since the temperature sensors 41, 41 and 43 are non-contact sensors, they can be permanently located in the foam materiel 27 and will be correctly positioned to sense the temperatures of those locations on the secondary 16 since they will always align with the opening in the plastic material 42 at the blackened areas of the secondary 16. As such, those temperature sensors 40, 41 and 43 can be calibrated for the particular heating device 10 and will correctly sense the desired temperatures at the known locations even with differing cartridges 30 since the construction of the cartridges 30 have uniform temperature sensed areas.

As can be seen in FIG. 3, the secondary 16 of the heater device 10 is basically a cartridge 30 that is self-contained and encased within the plastic material 42. It can easily be inserted into and removed from the receiver opening 28 so as to be operative or non-operative with respect to the primary windings 14. The cartridge 30 can be readily removed from the core 12 for cleaning, such as autoclaving, and, during that cleaning process, another cartridge may be used with the heating device by simply inserting that alternate cartridge into the receiver opening 28. To better facilitate the insertion and removal of the cartridges 30, the thickness of the cartridge 30 may be slightly tapered in the direction that it is inserted into the receiver opening 28.

When the cartridge 30 is inserted, there is a gap that is present between the secondary 16 and is basically due to the thickness of the plastic material 42 that provides the coating around the cartridge 30. That coating may be about 25 mils and which separates the inner legs 24 of the core sections 18, 20 from directly contacting the secondary 16. That gap is basically compensated for by the use of the ferrite insert 38 that is molded into the cartridge 30 and located within the interior of the elongated loop of the secondary 16.

Figure 4:
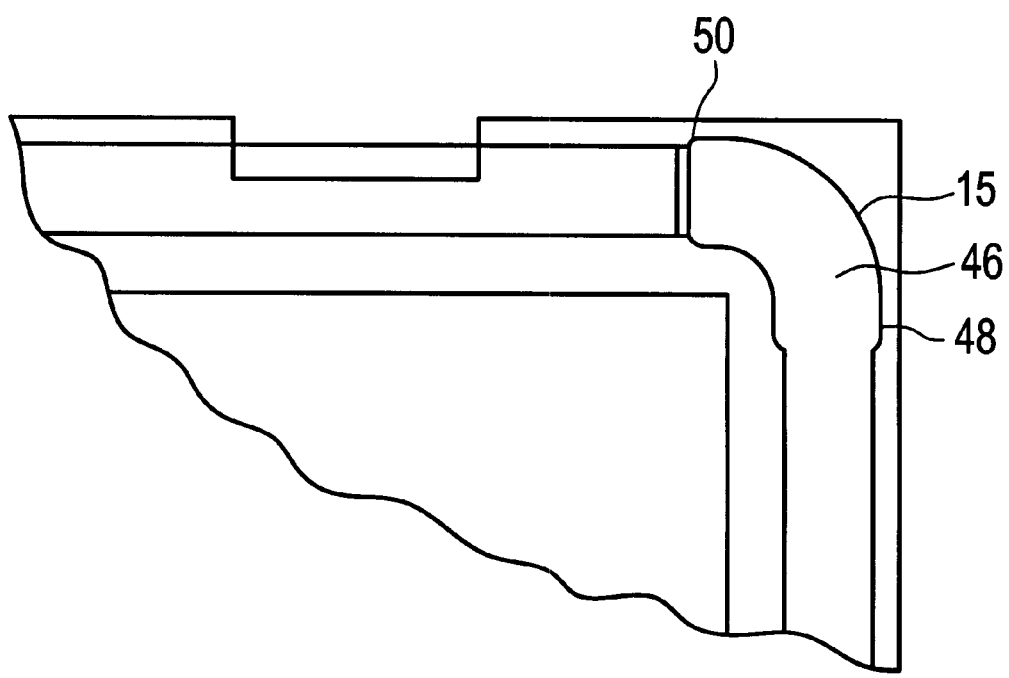
FIG. 4 is an enlarged fragmentary view of a portion of the secondary used with the present invention.

Turning now to FIG. 4, there is shown an enlarged fragmentary view of one of the abrupt corners 15 that is formed in the secondary 16 for the torturous path through which the fluid travels in passing through the secondary 16 during the heating process. As seen, the corner 15 has a enlarged diameter area 46 that commences at the entrance 48 to the corner 15, that is where the fluid begins to turn from its otherwise straight travel and an exit 50 where the fluid returns to its straight path. The corner 15 shown in FIG. 4 is typical of the plurality of curves that are formed in the secondary 16 to prevent laminar flow and to promote mixing of the fluid to insure that it is isothermic as it leaves the fluid heater 10. If the curves were not enlarged in diameter, it is possible for the fluid to build up a sound barrier and upset the flow of the fluid. In addition, the fluid could otherwise cavitate as it passes around a curve and move away from the internal surface of the wall of the secondary 16 and allow the inner wall to overheat and possibly reach an unacceptably high temperature. Accordingly, the enlargement in diameter increases that diameter by about t 15 percent to alleviate the aforementioned difficulties.

Figure 5:
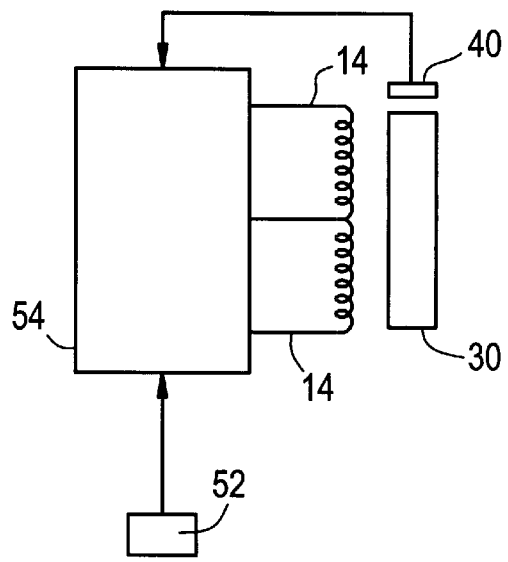
FIGS. 5 and 5A are electrical schematic views of the present invention.
Figure 5A:
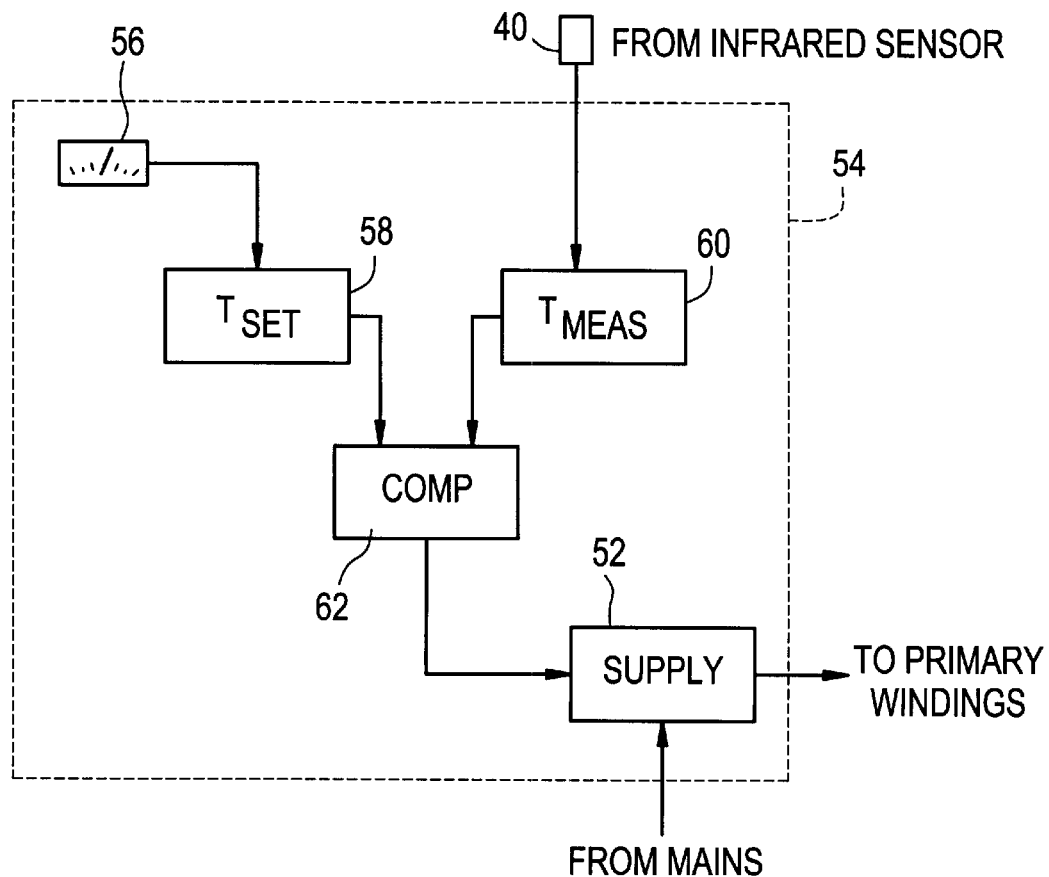

Turning now to FIGS. 5 and 5A, there are shown various schematic views of a control scheme that can be used by the present fluid heater 10 to control the temperature of the fluid that is delivered from the device. In particular, in FIG. 5, a power source 52 is connected to a controller 54 that is used to control the power to the primary windings 14 of the heating device 10. It is preferred that that power supply provide a very high frequency power in the range of about 50 Khz. With the high frequency, the frequency is well beyond the auditory drop-off frequency and is not heard by the patient, be that patient a human subject or an animal. The frequency is particularly important for use of the present heating device 10 with an animal where the lower frequencies can annoy or disturb the animal during use of the heating device. The use of the high frequency also allow the overall size of the transformer of the heating device 10 to be relatively small, thereby allowing the heating device 10 to be very portable for the convenience of the user. Also, because the use of a high frequency requires the use of small wires that take advantage of the skin effect, the wire used for the primary windings can be of a small diameter, such as Litz wire, that is accordingly very flexible and easy to wrap about the core sections.

In any event, in FIG. 5, the infrared sensor 40 senses the temperature of the secondary and uses that sensed temperature in the control schematic of FIG. 5A to control the temperature of the fluid to that desired by the user. Accordingly, in FIG. 5A, there is a manual input device 56 by which the user can manually enter the desire temperature for the fluid. The temperature from the manual input 56 is inputted to a register 58. A signal from the infrared sensor 40 is also received by the controller 54 and is inputted to a temperature module 60. The two temperatures are then compared in a comparator 62 where the sensed and measured temperatures are compared and a differential signal representative of the difference in those temperatures is inputted to the power supply 52 where the signal to the primary windings is adjusted to control the power supplied to the heating device 10 to attain the desired temperature of fluid.

Figure 6:
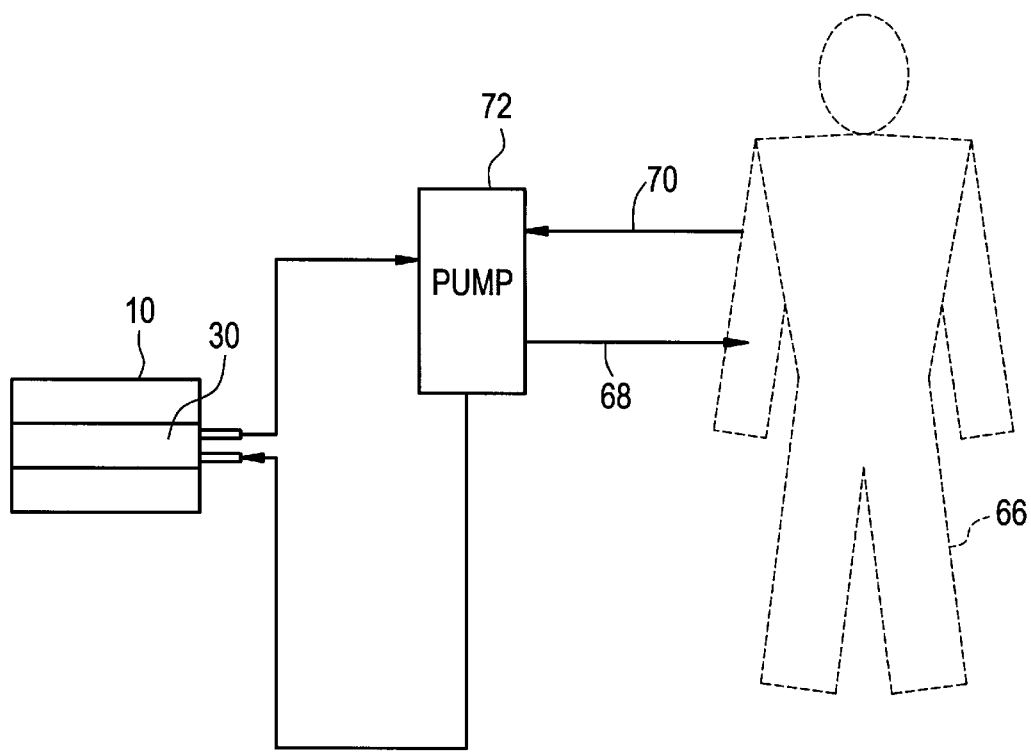
FIG. 6 is a schematic view of the use of the present invention to supply fluid to a patient.

Finally, turning to FIG. 6, there is shown a schematic view of the fluid heater 10 of the present invention used in a system to supply fluids to a patient. In FIG. 6, the patient 66 is a human, however, the present invention has wide applicability for animals as well since it is capable of supplying a flow of fluid at the temperature needed for the infusion of fluids into living entities as well as good control of the temperature of that fluid. Thus, as shown in the FIG. 6, there is a flow of fluid to the patient 66 for some form of therapy by means of a conduit 68 and a return flow of the fluid through a similar conduit 70. A pump 72 is used to pump that fluid into and out of the patient 66 and that pump 72 receives the fluid at the desired elevated temperature from the fluid heater 10 of the present invention. Thus, there is a closed system that can continually provide a heated flow of a fluid at a desired temperature. There may, of course, also be a reservoir of the fluid and that system may be changed or modified for a particular system that is used to supply a particular fluid to the patient 66, whether that fluid be blood during a trauma situation, or other fluids to carry out some treatment to the patient.

Accordingly, the present invention may be embodied in other forms without departing from the spirit or essential characteristics thereof. The embodiments disclosed in this application are to be considered as illustrative and not restrictive, the scope of the invention being indicated by the appended claims rather than by the foregoing description, and all changes which come within the meaning and range of equivalency of the claims are intended to be embraced therein.

I claim:

1. A heater for warming a fluid, said heater comprising:
   a transformer, said transformer having a core, a primary winding associated with said core and adapted to generate an alternating magnetic field in the presence of an alternating power passing through said primary winding and a secondary winding,
   a secondary cartridge interfitted into said core, said secondary cartridge enclosing the secondary winding comprising a metallic conduit having an inlet and an outlet for passing a fluid through said secondary cartridge, said secondary cartridge, when interfitted into said core, being located in the alternating magnetic field to produce induced currents in said secondary winding, said secondary winding being shorted out to convert the induced currents into heat to heat a fluid passing therethrough,
   wherein said secondary cartridge is readily removed from the interfitting relationship with said core.

2. The heater as defined in claim 1 wherein said core has an opening therein and said secondary cartridge interfits into said opening.

3. The heater as defined in claim 1 wherein said secondary cartridge comprises a housing having said metallic conduit embedded therein.

4. The heater as defined in claim 3 wherein said metallic conduit comprises an elongated loop configuration wherein said elongated loop is electrically connected to create an electrical short at about said inlet and said outlet.

5. The heater as defined in claim 3 wherein said metallic conduit has an internal surface coated with a lubricious film.

6. The heater as defined in claim 5 wherein said metallic conduit has an internal surface coated with parylene.

7. The heater as defined in claim 3 wherein said heater has at least one temperature sensor affixed with respect to said core, said at least one temperature sensor adapted to directed energy toward said metallic conduit and to receive energy reflected therefrom to sense the temperature of at least one area of said conduit.

8. The heater as defined in claim 7 wherein said heater has three temperature sensors adapted, respectively, to direct the energy toward and receive reflected energy from areas of said conduit near said inlet, near said outlet and about an area equidistant between said inlet and said outlet.

9. A transformer secondary cartridge for removably interfitting with a transformer core having a primary winding, said transformer secondary cartridge comprising a housing, a conduit contained within said housing and being comprised at least partially of an electrical conducting material, said conduit having an inlet and an outlet for supplying a fluid to and for receiving fluid from said conduit, said conduit forming an elongated, generally planar loop and being shorted out near said inlet and said outlet whereby said transformer secondary cartridge is self-contained and is readily attachable and detachable from a transformer core having a primary.

10. The transformer secondary cartridge as defined in claim 9 wherein said conduit is a tubular thin-walled ferrous material.

11. The transformer secondary cartridge as defined in claim 10 wherein said tubular thin-walled ferrous conduit is stainless steel having a wall thickness of about 0.004 to 0.006 inches.

12. The transformer secondary cartridge as defined in claim 9 wherein said conduit is embedded in said housing.

13. The transformer secondary as defined in claim 9 wherein said conduit has an internal surface coated with a lubricious film.

14. The transformer secondary as defined in claim 13 wherein said lubricious film is parylene.

15. The transformer secondary as defined in claim 9 wherein said elongated, generally planar loop of said secondary comprises a loop having a plurality of abrupt curves in excess of 45 degrees.

16. The transformer secondary as defined in claim 15 wherein said elongated loop has at least 6 abrupt curves.

17. The transformer secondary as defined in claim 15 wherein each of said abrupt curves comprises an expanded diameter between an entrance to an abrupt curve and an end point of the abrupt curve.

18. A heater for warming a fluid, said heater comprising:

a pair of E-shaped transformer core sections, each of said E-shaped core sections having outer legs and an inner leg, said inner leg of each of said core sections being shorter in length that said outer legs, a primary winding wound around each of said core sections, said core sections being positioned such that said outer legs of one of said core section is located contiguous to the outer legs of said other core section, each of said primary windings adapted to generate an alternating magnetic field in the presence of an alternating power passing through each of said primary windings, said pair of primary windings being enclosed with a potting material and forming a receiver opening intermediate said inner legs of said core sections, a secondary cartridge interfitted into said receiver opening, said secondary cartridge including a thin-walled, metallic conduit having an inlet and an outlet for passing a fluid through said secondary cartridge, said secondary cartridge, when interfitted into said receiver opening, being located in the alternating magnetic field to produce induced currents in said metallic conduit, said thin-walled metallic conduit acting as a secondary winding to said primary winding and being shorted out to convert the induced currents into heat to heat the fluid passing therethrough, said secondary cartridge being readily removed and reinserted into said receiver opening.

19. The heater for warming a fluid as defined in claim 18 wherein said secondary cartridge is comprised of a plastic material enclosing said thin-walled metallic conduit.

20. The heater for warming a fluid as defined in claim 18 wherein said thin-walled metallic conduit is formed in the configuration of an elongated loop.

21. The heater for warming a fluid as defined in claim 18 wherein said thin-walled metallic conduit has an interior surface coated with a film of a lubricious material.

22. The heater for warming a fluid as defined in claim 18 wherein said plastic material is a glass filled polyetheramide composition.

23. The heater for warming a fluid as defined in claim 18 wherein said metallic conduit is a stainless steel conduit having a wall thickness of about 0.004 to 0.006 inches.

24. The heater for warming a fluid as defined in claim 18 wherein said metallic conduit is a planar, elongated loop having a plurality of abrupt curves.

25. The heater for warming a fluid as defined in claim 24 wherein said thin-walled metallic conduit has a predetermined diameter and wherein said abrupt curves have an increased diameter with respect to said predetermined diameter.

26. The heater for warming a fluid as defined in claim 18 wherein said secondary winding is shorted out by means of a weld joining said elongated loop together at a point near said inlet and said outlet.

27. The heater for warming a fluid as defined in claim 26 wherein said weld has a weld area and said weld area is at least 2 times the cross sectional area of said metallic conduit.

28. The heater for warming a fluid as defined in claim 19 wherein said heater includes at least one temperature sensor in a potting material, said at least one temperature sensor being adapted to sense the temperature of at least one area of said metallic conduit.

29. The heater for warming a fluid as defined in claim 28 wherein said at least one temperature sensor comprises three temperature sensors adapted to sense, respectively, the temperature of said thin-walled metallic conduit at an area near said inlet, an area near said outlet and an area about equidistant between said inlet and said outlet.

30. The heater for warming a fluid as defined in claim 28 wherein said at least one area of said conduit comprises at least one blackened area of the external surface of said conduit.

31. The heater for warming a fluid as defined in claim 30 wherein said temperature sensor is an infrared sensor and said plastic material surrounding said secondary has at least one opening corresponding to said at least one blackened area to allow infrared energy from said temperature sensor to impinge upon and be reflected from said at least one blackened area.

32. The heater for warming a fluid as defined in claim 30 wherein said at least one area of said conduit comprises three areas located at, respectively, near said inlet, near said outlet and about equidistant between said inlet and said outlet.

33. The heater for warming a fluid as defined in claim 19 further including a pair of transition blocks comprised of a low magnetic permeability material located in contact with and spanning the lateral external surfaces of said core sections.

* * * * *